(12) United States Patent
Kayser et al.

(10) Patent No.: US 6,861,258 B2
(45) Date of Patent: Mar. 1, 2005

(54) **SYSTEM AND METHOD FOR INTRODUCTION AND STABILIZATION OF GENES IN *THERMUS* SP.**

(75) Inventors: Kevin J. Kayser, Woodstock, IL (US); Ho-Shin Park, Chicago, IL (US); John J. Kilbane, II, Woodstock, IL (US)

(73) Assignee: Gas Technology Institute, Des Plaines, IL (US)

( * ) Notice: Subject to any disclaimer, the term of this patent is extended or adjusted under 35 U.S.C. 154(b) by 21 days.

(21) Appl. No.: 10/085,388

(22) Filed: Feb. 28, 2002

(65) Prior Publication Data

US 2003/0170900 A1 Sep. 11, 2003

(51) Int. Cl.[7] .......................... C12N 15/74; C12N 1/21; C12P 21/00
(52) U.S. Cl. .................. 435/476; 435/252.3; 435/71.2
(58) Field of Search ............................. 435/476, 252.3, 435/71.2, 477, 479

(56) References Cited

U.S. PATENT DOCUMENTS 5,491,079 A * 2/1996 Knol et al. .................. 435/6
6,344,327 B1 2/2002 Peredultchuk et al.
6,350,591 B1 2/2002 Weber et al.

OTHER PUBLICATIONS

Kayser et al., J. Bacteriol., vol. 183, No. 5, pp. 1792–1795 (2001).*
Tamakoshi et al., J. Bacterol. 179 (15), pp. 4811–4814 (1997).*
Mollet et al., J. Bacteriol. 175 (14), pp. 4315–4324 (1993).*
Nishiyama et al., J. Biol. Chem, 261 (30), 14178–14183 (1986).*

* cited by examiner

*Primary Examiner*—Terry McKelvey
*Assistant Examiner*—Nancy T. Vogel
(74) *Attorney, Agent, or Firm*—Mark E. Fejer

(57) ABSTRACT

A method for introducing and stabilizing heterologous and recombinant genes in a thermophilic host in which a characteristic gene defining a detectable host characteristic is inactivated or deleted from the thermophilic host, resulting in a modified thermophilic host expressing an absence of the detectable host characteristic. A DNA fragment of interest is inserted into the modified thermophilic host together with an intact characteristic gene, whereby the detectable host characteristic is restored to the thermophilic host, thereby enabling detection and confirmation of successful transformation using plasmid vectors and integration of the DNA fragment into the chromosome of the thermophilic host.

4 Claims, 9 Drawing Sheets

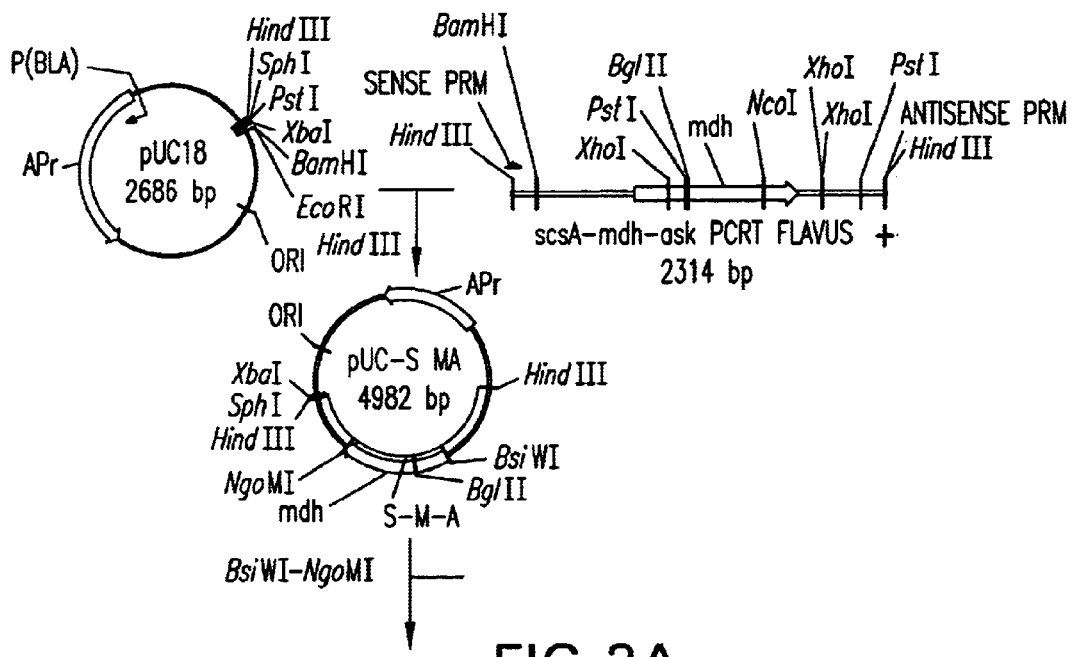
FIG.2A
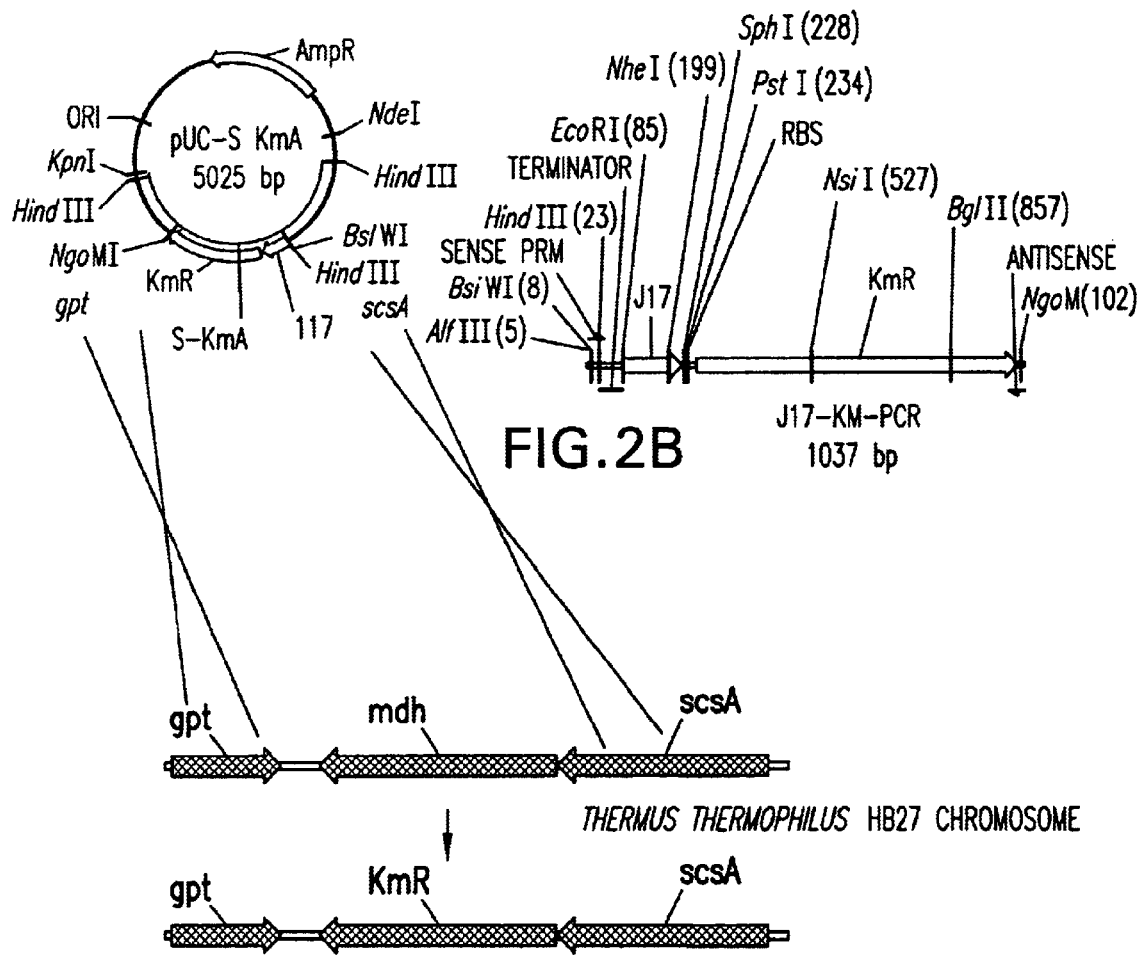
FIG.2B
FIG.2C

SEQUENCE LISTING

<160> NUMBER OF SEQ ID NOS: 10

<210> SEQ ID NO 1
<211> LENGTH: 31
<212> TYPE: DNA
<213> ORGANISM: Artificial
<220> FEATURE:
<223> OTHER INFORMATION: PCR Primer

<400> SEQUENCE: 1
acacaccata tgctcggcgt ttgctattac c                31

<210> SEQ ID NO 2
<211> LENGTH: 33
<212> TYPE: DNA
<213> ORGANISM: Artificial

-continued

```
<220> FEATURE:
<223> OTHER INFORMATION: PCR Primer

<400> SEQUENCE: 2
gcggcagacc cgccgccgta caagcttaca cac                         33

<210> SEQ ID NO 3
<211> LENGTH: 30
<212> TYPE: DNA
<213> ORGANISM: Artificial
<220> FEATURE:
<223> OTHER INFORMATION: PCR Primer

<400> SEQUENCE: 3
acacacttta aacatggcct aatgccaccc                             30

<210> SEQ ID NO 4
<211> LENGTH: 30
<212> TYPE: DNA
<213> ORGANISM: Artificial
<220> FEATURE:
<223> OTHER INFORMATION: PCR Primer

<400> SEQUENCE: 4
ttgtgtttta aatcaaaatg gtatgcgttt                             30

<210> SEQ ID NO 5
<211> LENGTH: 29
<212> TYPE: DNA
<213> ORGANISM: Artificial
<220> FEATURE:
<223> OTHER INFORMATION: PCR Primer

<400> SEQUENCE: 5
acacacctta agggtgtcc ccggcgcgc                               29

<210> SEQ ID NO 6
<211> LENGTH: 28
<212> TYPE: DNA
<213> ORGANISM: Artificial
<220> FEATURE:
<223> OTHER INFORMATION: PCR Primer

<400> SEQUENCE: 6
acacaccata tgacgtcttc acctcgcc                               28

<210> SEQ ID NO 7
<211> LENGTH: 33
<212> TYPE: DNA
<213> ORGANISM: Artificial
<220> FEATURE:
<223> OTHER INFORMATION: PCR Primer

<400> SEQUENCE: 7
acacacctta aggcttaagg aattctggcc gcc                         33

<210> SEQ ID NO 8
<211> LENGTH: 30
<212> TYPE: DNA
<213> ORGANISM: Artificial
<220> FEATURE:
<223> OTHER INFORMATION: PCR Primer

<400> SEQUENCE: 8
acacaccata tgccttatca ccttcctttt                             30
```

```
<210> SEQ ID NO 9
<211> LENGTH: 29
<212> TYPE: DNA
<213> ORGANISM: Artificial
<220> FEATURE:
<223> OTHER INFORMATION: PCR Primer

<400> SEQUENCE: 9
acacacctta agaattgctg gatggcctc                                   29

<210> SEQ ID NO 10
<211> LENGTH: 30
<212> TYPE: DNA
<213> ORGANISM: Artificial
<220> FEATURE:
<223> OTHER INFORMATION: PCR Primer

<400> SEQUENCE: 10
acacaccata tggacccacc tcccttgccg                                  30
```

SYSTEM AND METHOD FOR INTRODUCTION AND STABILIZATION OF GENES IN *THERMUS* SP.

This invention was made with Government support under Prime Contract No. DE-FG02-97ER62464 awarded by the Department of Energy. The Government has certain rights in this invention.

BACKGROUND OF THE INVENTION

Field of the Invention

This invention is related to a method and system for introducing and stabilizing heterologous and recombinant genes in *Thermus* sp. This invention further relates to host-vector systems for *Thermus* sp. based upon characteristic genes that define a detectable host characteristic. More particularly, this invention relates to host-vector systems for *Thermus* sp. based upon the malate dehydrogenase gene, the phytoene dehydrogenase gene and the β-galactosidase gene.

*Thermus* sp. are thermophilic microorganisms that can survive in extreme environments with temperatures as high as 90° C. Because of the high growth temperature, reaction rates are faster and thermostable enzymes/proteins are more durable/resilient in industrial processes than mesophilic enzymes/proteins.

High level expression of cloned genes is often achieved in *E. coli, Bacillus subtilis* and other well studied microorganisms by the use of high copy number plasmid vectors. Besides high copy number, plasmid expression vectors have an advantage in comparison with integrative vectors of being easier to recover/purify from the host strain so that subsequent genetic modifications can be conveniently performed. However, plasmids are less stable than genes integrated into the chromosome of a host and plasmid instability is thought to be of particular concern in *Thermus* hosts where growth temperatures of 55° C. to 82° C. are routine. Another disadvantage of plasmid versus integrative vectors for use in *Thermus* sp. is that plasmid vectors generally have from 10 to 1,000-fold lower transformation efficiencies than integrative vectors. Consequently, integrative vectors are frequently used in genetic studies of *Thermus* sp.

Plasmid vectors that have been used in *Thermus* sp. have been constructed that encode tryptophan, leucine or pyrimidine synthesis genes to complement auxotrophic and deleted hosts, thereby providing for positive selection of transformants. However, such expression vectors were cumbersome to use because they do not provide a wide choice of convenient cloning sites, choice of promoters and ribosomal binding sites, nor do they provide a convenient in vivo means of monitoring transcription of the cloned gene(s).

SUMMARY OF THE INVENTION

Accordingly, it is one object of this invention to provide a method and system for convenient in vivo means of monitoring transcription of cloned genes in *Thermus* sp. By "convenient", we mean methods and systems employing vectors which provide a wide choice of convenient cloning sites, a choice of promoters and ribosomal binding sites, visual confirmation of transformation, and simple quantification of gene expression.

This and other objects of this invention are addressed by a method for introducing and stabilizing heterologous and recombinant genes in a thermophilic host in which a characteristic gene defining a detectable host characteristic is inactivated in or deleted from the thermophilic host, resulting in a modified thermophilic host expressing an absence of the detectable host characteristic. A DNA fragment of interest is introduced into the modified thermophilic host together with an intact said characteristic gene, whereby the detectable host characteristic is restored to the thermophilic host, thereby enabling detection and confirmation of successful transformation of a plasmid or integration of the DNA fragment into the chromosome of the thermophilic host. The detectable host characteristic is deleted or diminished in activity by suitable integration vectors. Colonies resulting from transformation of these vectors into wild type *Thermus* cultures are recognized by an insertional inactivation of the detectable host characteristic. Such modified cultures can then be used as recipients in future transformation experiments.

In accordance with one embodiment of this invention, an integrative vector is employed that deletes or diminishes the malate dehydrogenase (mdh) gene activity in *Thermus* sp. Colonies resulting from transformation of this vector into wild type *Thermus* cultures are recognized by an insertional inactivation of the malate dehydrogenase gene that yields a "sick" colony phenotype. In accordance with another embodiment of this invention, an integrative vector is employed that deletes or diminishes phytoene dehydrogenase gene activity in *Thermus* sp. Colonies resulting from transformation of this vector into wild type *Thermus* cultures contain deleted or inactivated dehydrogenase genes, which can only be white in color and which are recognized by changes in color relative to those colonies in which the phytoene dehydrogenase gene is intact. In accordance with yet another embodiment of this invention, vectors that delete or diminish the activity of the *Thermus* β-galactosidase gene are employed and colonies resulting from transformation of this vector are also recognized by differences in color as well as by enzymatic assays.

BRIEF DESCRIPTION OF THE DRAWINGS

These and other objects and features of this invention will be better understood from the following detailed description taken in conjunction with the drawings wherein:

FIG. 2 is a diagram showing the construction of *Thermus thermophilus* MM8-5 that contains a deletion of the mdh gene. In step A, a PCR fragment containing the *T. flavus* mdh gene along with several hundred base pairs of 5' and 3' flanking regions (scsA and gpt, respectively) is cloned into pUC18 to create pUC-SMA. Then, in step B, a DNA fragment containing a kanamycin resistance gene under the control of a *Thermus* promoter, J17, is cloned into pUC-SMA, replacing the BsiWI/NgoMI fragment that contains the mdh gene to create pUC-SKmA, which, in step C, is introduced into *T. thermophilus* where a double crossover homologous r5ecombination results in the replacement of the chromosomal mdh gene with a kanamycin resistance gene;

FIG. 4 shows the cloning of a PCR fragment containing the *Thermus* phyD gene into *E. coli* vector pGEMT-easy to create pGEM-phyD, which was digested with BglII and KpnI to remove a control portion, but not all, of the phyD gene to yield pGEM-phyD trunc. When pGEM-phyD trunc is introduced into *Thermus*, homologous recombination allows insertional inactivation or deletion of a portion of the phyD gene in the chromosome of a *Thermus* host, which can be recognized by colonies that are devoid of pigmentation;

FIG. 5 illustrates pTEXI-phyD which contains genes allowing replication in both *E. coli* and *Thermus* and contains the phyD gene under the control of *Thermus* promoter J17;

FIG. 6 shows the cloning of a 1968 bp PCR fragment containing the β-galactosidase gene along with several hundred base pairs of 3' and 5' flanking sequences into *E. coli* plasmid pUC18 to create pUC 18P-G-U. Plasmid pUC18P-G-U is then digested with EcoRI and KpnI to remove a 1320 bp fragment containing the β-galactosidase gene, which is replaced by a 1019 bp fragment containing the kanamycin resistance gene under the control of *Thermus* promoter J17 to yield pUC18P-Km-U. When pUC18P-Km-U is introduced into a *Thermus* host, a double crossover homologous recombination results in the deletion of the chromosomal β-galactosidase gene and its replacement with the kanamycin resistance gene;

FIG. 7 shows the construction of a hybrid replicon resulting from the combination of the *Thermus/E. coli* shuttle vector pMK18 with *E. coli* plasmid pUC18 and PCR fragments containing the *Thermus* β-galactosidase gene and a *Thermus* promoter (PdnaK, Parg, Pscs-mdh, or other promoters) to yield pTEX5β-gal, or a related plasmid. Subsequently, the kanamycin resistance gene under the control of a *Thermus* promoter is added to the vector to facilitate the isolation of transformants in *Thermus*;

DETAILED DESCRIPTION OF THE PRESENTLY PREFERRED EMBODIMENTS

The invention disclosed and claimed herein is a method for introducing and stabilizing heterologous and recombinant genes in thermophilic hosts employing host-vector systems comprising a thermophilic host strain in which a detectable host characteristic gene is inactivated or deleted resulting in a change in the host strain phenotype and an integrative or plasmid vector comprising an intact detectable characteristic gene and a gene of interest for insertion into the thermophilic host. Deletion of the mdh locus is accomplished by constructing a kanamycin resistance gene cassette in which the kanamycin gene is flanked by DNA sequences homologous to those DNA sequences that flank the mdh gene in the *Thermus* chromosome. The length of these flanking homologous regions is from 50 bp to 1,000 bp or more. The kanamycin resistance gene cassette has no ability to replicate autonomously in *Thermus* so when it is introduced into *Thermus* by natural transformation or electroporation selection for kanamycin resistant transformants results in the isolation of cultures in which homologous recombination has resulted in the deletion of the mdh gene and substitution of the kanamycin resistance gene as shown in FIG. 1.

Figure 1:
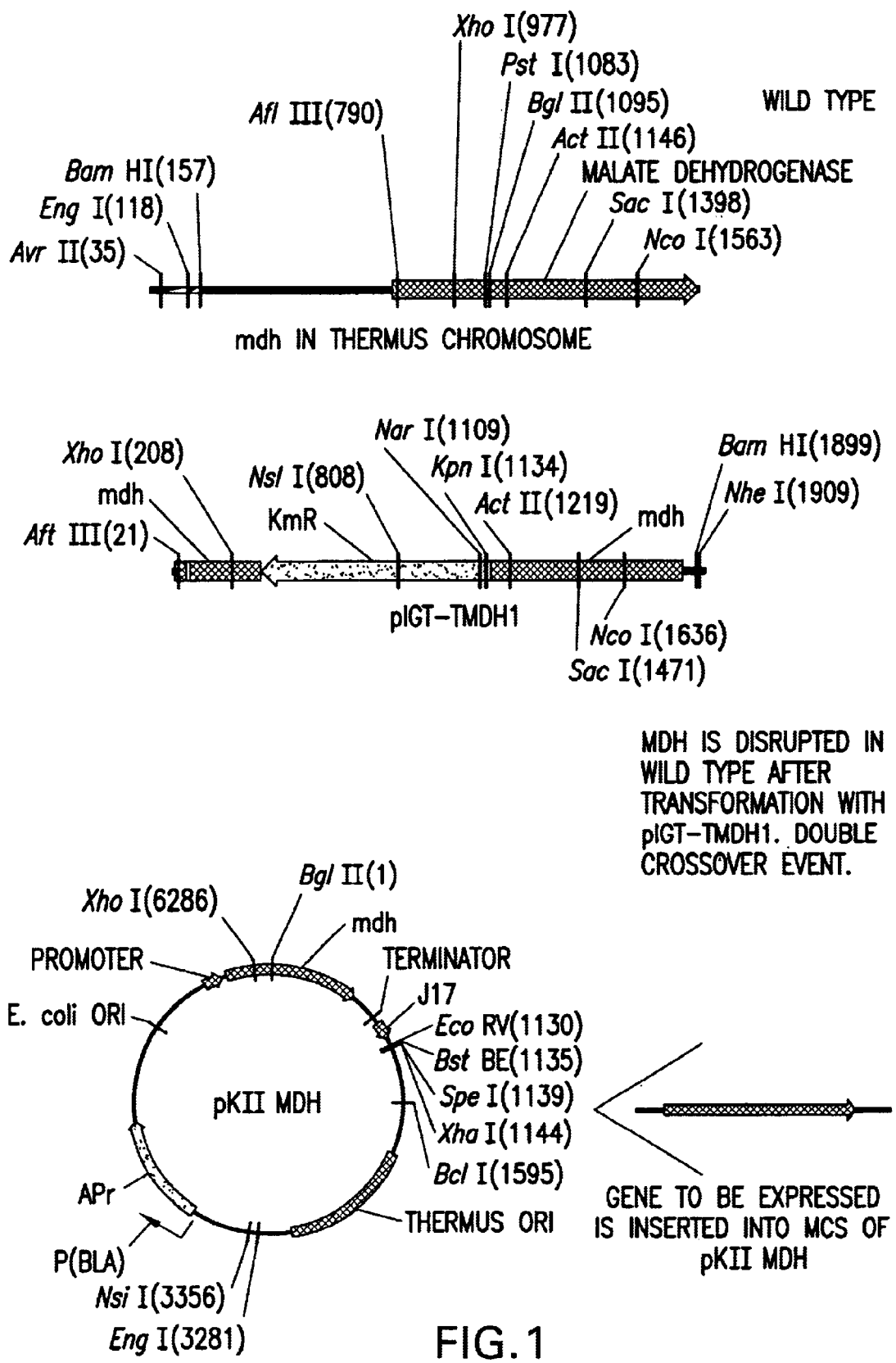
FIG. 1 is a diagram showing the method for introducing and stabilizing heterologous and recombinant genes in a thermophilic host in accordance with one embodiment of this invention. More particularly, FIG. S is a schematic illustration of stabilizing a plasmid containing an mdh gene by use of a *Thermus* host that lacks an mdh gene.

In accordance with one embodiment of the method of this invention as shown in FIG. 1, the detectable characteristic gene is the malate dehydrogenase gene, which, when rendered inactive in the *Thermus* sp., produces a "sick" colony phenotype. The "healthy" phenotype is restored by introduction/transformation of a plasmid, integration vector or DNA fragment containing an intact mdh gene as well as a gene of interest. The intact mdh gene complements the non-functional mdh gene in the thermophilic host. This provides for a reliable and convenient means of detecting and confirming the integration of homologous, and associated heterologous, DNA into the chromosome of the thermophilic host. Maintenance of the intact mdh gene is required for healthy growth of the culture and, in turn, stabilizes the introduced gene of interest. In addition, by cloning the gene of interest adjacent to the mdh gene in the plasmid or integrative vector, any gene of interest can be introduced and maintained in a stable manner in *Thermus*. This is particularly useful for genes for which there is no convenient selection and this invention insures that a gene of interest will be stably maintained in the *Thermus* host, thereby overcoming a major problem in the production of biotechnology products.

As shown in FIG. 1, the mdh gene in a *Thermus* chromosome (wild type) is disrupted after transformation with pIGT-TMDH1 in a double cross-over event. pKII MDH, shown in FIG. 1, is a *Thermus* plasmid that carries a functional mdh gene downstream of a *Thermus* promoter. A multiple cloning site (MCS) site downstream of an additional strong *Thermus* promoter allows for cloning and expression of genes of interest for the formation of biotechnology products. Any gene of interest can be cloned into the MCS and expressed by the strong *Thermus* promoter located immediately upstream. This vector and its derivatives are stably maintained in *Thermus* hosts that lack a functional mdh gene.

In accordance with one embodiment of this invention, the plasmid pKII MDH is modified to delete the *Thermus* replication genes. As a result, this plasmid can only replicate in E. coli but not in Thermus hosts. However, this plasmid can be introduced into Thermus hosts and because it contains regions of DNA that are homologous to regions of DNA in the chromosome of Thermus, homologous recombination can result in the integration of this plasmid into the chromosome of Thermus allowing it to be replicated/maintained as a portion of the chromosome. This is a single crossover integration vector. A multiple cloning site downstream of a strong Thermus promoter allows for cloning and expression of genes for the formation of biotechnology products. Any region of homology of the Thermus chromosome can be used provided it has a size equal to or greater than 50 bp of DNA. Similar integrative vectors can be constructed that contain two regions of homology with the Thermus chromosome flanking the mdh gene and the gene of interest. Such plasmids can integrate into the chromosome of Thermus hosts by a double crossover event. Single crossover integrative plasmids result in the integration of the entire plasmid into the chromosome of the host while double crossover integrative vectors result in the integration of only those genes flanked by homologous sequences.

In this example, a Thermus thermophilus HB27 strain was constructed in which the malate dehydrogenase gene was deleted. Construction of this strain is shown in FIG. 2. To create the Δmdh strain of T. thermophilus HB27, we constructed an integration vector designated pUC-S KmA. A 2.3-kb PCR fragment containing a region spanning three separate genes, succinate coenzyme A ligase (scsA), malate dehydrogenase (mdh), and purine phosphoribosyltransferase (gpt), was amplified from the T. flavus chromosome and cloned into pUC18. A 10-ul PCR amplification reaction was conducted in an Idaho Technologies Rapid Air Thermo-Cycler in the presence of 8% glycerol and 1% dimethyl sulfoxide. The PCR amplification program was run for 40 cycles at 94° C., 55° C., and 1 min of holding at 72° C. The 984-bp mdh gene is located near the center of this 2.3-kb fragment, so that the chromosomal regions that flank mdh are 780 bp (5') and 560 bp (3'). The entire coding sequence of the mdh gene was removed by restriction enzymes and replaced with a thermotolerant kanamycin resistance cassette ($Km^r$). This vector, designated pUC-SKmA, can replicate in E. coli but not in Thermus. However, homologous recombination between the scsA and gpt gene sequences allowed pUC-SKmA to integrate into the chromosome when it was used to transform T. thermophilus HB27. Transformants were screened at 55° C. on TT rich medium supplemented with kanamycin (40 µg/ml). Approximately $10^4$ kanamycin-resistant transformants per µg of DNA were observed. Two distinct colony types arose after 5 days of incubation. The majority of the colonies were very small (0.1 to 0.5 mm) even after 5 days. A few colonies (60 to 100 CFU) were much larger (1.5 to 2.8 mm), the same size as wild-type T. thermophilus HB27 colonies. The two colony types were subcultured, and total DNA (plasmid and chromosomal) was dot blotted onto a nylon membrane.

The dot blot was probed with a digoxigenin-11-dUTP (DIG)-labeled T. flavus mdh gene. DNA prepared from the smaller colonies did not hybridize to the T. flavus mdh gene, whereas DNA harvested from the larger colonies hybridized to the mdh probe. The membrane was also probed with a DIG-labeled $Km^r$ cassette, and both small and large colony types hybridized to it. Because malate dehydrogenase is a key enzyme in the tricarboxylic acid cycle, the colonies resulting from double-crossover integration events (Δmdh) are recognized by this small-colony phenotype. The larger $Km^r$ colonies were single-crossover integration events in which the chromosomal mdh is intact and the entire plasmid is in the chromosome. The T. thermophilus Δmdh $Km^r$ mutant strain was designated MM8-5. T. thermophilus Δmdh $Km^r$ MM8-5 was used as a recipient in further transformation experiments.

Figure 3A:
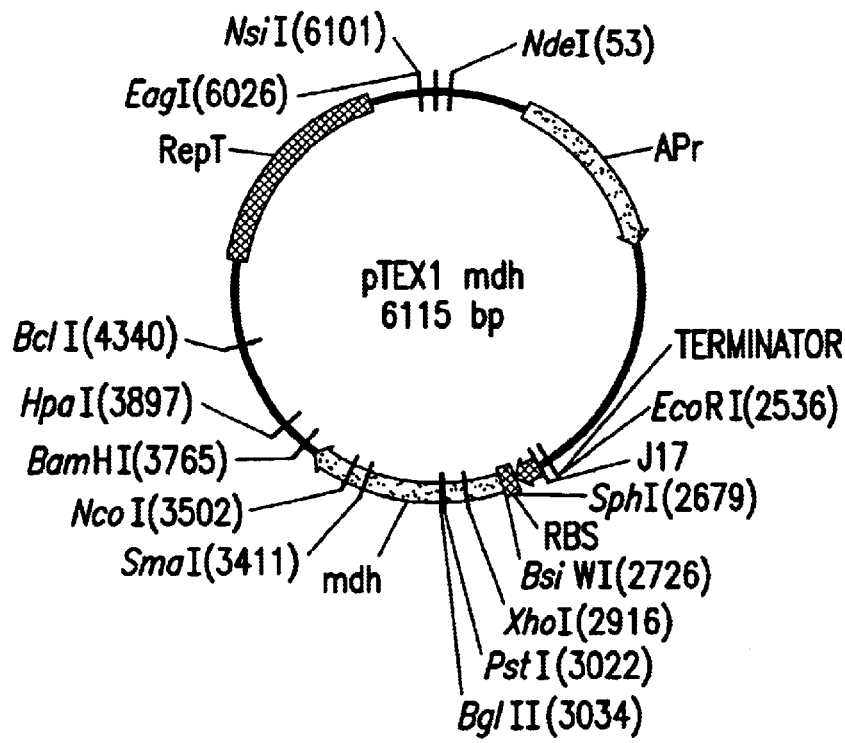
FIG. 3 shows the construction of plasmid and integrative vectors for expression of the mdh gene in *Thermus* species. Part A illustrates pTEXI mdh, which is a plasmid capable of replicating in *Thermus* and *E. coli* and which contains a complete mdh gene under the control of *Thermus* promoter J17 and a *Thermus* ribosome binding site. A transcriptional terminator is located just upstream from promoter J17. Part B illustrates integrative vector pSJ17mdhA, which can replicate in *E. coli* but not *Thermus*. It contains the mdh gene under the control of *Thermus* promoter J17, and the mdh contains several hundred base pairs of 5' and 3' flanking sequences (scgA and gpt, respectively) that allow homologous recombination with sequences in the *Thermus* chromosome when pSJ17mdhA is introduced into a *Thermus* host.

In this example, Thermus vectors containing mdh as a reporter gene were constructed in accordance with one embodiment of this invention. The malate dehydrogenase (mdh) gene from T. flavus was amplified by PCR and cloned into Thermus-E. coli expression vector pTEXI. The expression vector pTEXI is capable of replication in both Thermus sp. and E. coli, and the promoter (J17) employed in this expression vector functions in both bacterial hosts. J17 is a constitutive promoter isolated from T. thermophilus chromosomal DNA. The expression vector containing the mdh gene, designated pTEXI-mdh, is diagramed in FIG. 3A.

TABLE 1

Malate dehydrogenase activity of Thermus vector constructs

| Strain | Promoter expressing mdh | MDH activity (U/mg) 25° C. | 50° C. |
|---|---|---|---|
| HB27 | Wild type | 2.5 ± 0.12 | 19.9 ± 0.25 |
| MM8-5/pSJ17mdhA* | J17 | 0.6 ± 0.01 | 5.5 ± 0.17 |
| HB27/pTEX1-mdh | J17 | 3.7 ± 0.06 | 29.6 ± 1.39 |
| MM8-5 | None | 0.0 | 0.5 ± 0.01 |
| MM8-5/pTEX1-mdh | J17 | 4.2 ± 0.13 | 32.6 ± 0.72 |
| MM8-5/pTEX1-D50-3 | D50-3 | 0.3 | 2.7 ± 0.07 |
| MM8-5/pTEX1-P2-300 | P2-300 | 3.0 ± 0.07 | 23.2 ± 0.99 |

Figure 3B:
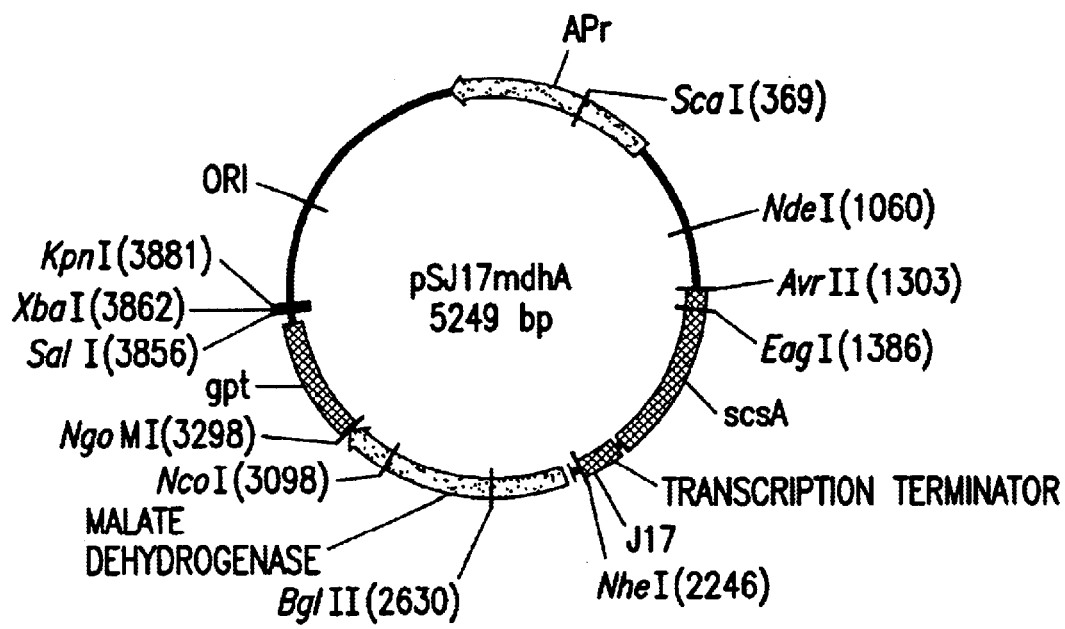

Activity values recorded are averages of three replicate samples from three separate experiments, for a total of nine data points. Standard deviation is less than 5%. One unit of activity is defined as the amount of enzyme needed to convert 1 µmol of NADH to NAD in 1 min. *, integrative vector The J17 promoter from pTEXI-mdh was replaced by two constitutive Thermus promoters isolated in our laboratory (D50-3 and P2-100). These promoters have low and medium levels of expression, respectively, in Thermus sp. relative to J17. The resulting plasmids were designated pTEX1-D50-3 and pTEX1-P2-100. An integrative vector was constructed to examine the expression of the mdh gene under control of the J17 promoter present as a single integrated copy. This construct was designated pSJ17mdhA and is shown in FIG. 3B. pSJ17mdhA contains pUC19 sequences and can replicate in E. coli. pSJ17mdhA does not replicate in Thermus sp. as a plasmid but integrates into the chromosome by a double-crossover event. pSJ17mdhA has the J17 promoter-mdh gene cassette flanked by the scsA and gpt chromosomal regions. A transcription termination sequence from the T. flavus phenylalanyl tRNA synthetase operon was cloned upstream of the cassette to prevent transcription read through from the native succinateCoA ligase/malate dehydrogenase operon promoter.

Plasmids pTEXI-mdh, pTEXI-D50-3, and pTEXI-P2-100 and the integrative vector pSJ17mdhA were transformed into MM8-5. Transformants were easily detected by the restoration of cultures to the wild-type or larger and faster-growing colonies by the expression of the malate dehydrogenase gene located on these expression vectors. Typically, T. thermophilus strain MM8-5 takes 4 to 5 days to form small visible colonies at 55° C. in TT supplemented with 40 µg of kanamycin per ml. However, T. thermophilus MM8-5 transformants that received an expression vector carrying the mdh gene yielded larger colonies in 2 to 3 days.

Expression vector pTEXI-mdh and the alternative promoter pTEX derivatives are very stable in T. thermophilus MM8-5. After more than 20 generations of growth under nonselective conditions, pTEX plasmids were detected in all of the colonies examined (100 for each species). This result is expected because *T. thermophilus* MM8-5 cells that possess expression vectors containing the mdh gene grow more rapidly than plasmid-free cells that lack a functional mdh gene.

The levels of malate dehydrogenase being produced by plasmid and integrative expression vectors were evaluated in both *T. thermophilus* HB27 and MM8-5. Crude lysates prepared from each culture were assayed for enzyme activity at two temperatures (25° C. and 50° C.), and the results are shown in Table 1. *T. thermophilus* MM8-5 had slight to no malate dehydrogenase activity, confirming complete deletion of the mdh gene from the chromosome of this strain. The activity observed in assays performed at 50° C. reflect a slight amount of background due to the conversion of NADH to NAD by unidentified components of cell lysates rather than the malate dehydrogenase-dependent conversion of oxaloacetate and NADH to malate and NAD.

The malate dehydrogenase activity of crude extracts assayed at 50° C. is on average nine times higher than the activity levels measured at 25° C. The data in Table 1 clearly indicate that promoters D50-3, P2-300, and J17 have different strengths, resulting in enzyme levels in MM8-5 strains that are 0.28, 1.16, and 1.65 times the level in wild-type *T thermophilus* HB27, respectively. Since each promoter is evaluated in identical genetic constructs that differ only by the promoter driving expression of the mdh gene, these levels serve to accurately quantify the strength of these promoters. Other strains whose enzyme activity is listed in Table 1 all use the same promoter, J17, to express the mdh gene in various backgrounds.

MM8-5/pS-J17mdh-A contains a single copy of the mdh gene integrated into the chromosome under the control of the J17 promoter. MM8-5/pTEXI-mdh contains the mdh gene under the control of the J17 promoter on a plasmid vector, and HB27/pTEXI-mdh contains two separate sources of the mdh gene, a wild-type mdh gene on the chromosome and the mdh gene under the control of the J17 promoter on a plasmid vector. Since MM8-5/pTEXI-mdh yields 32.6 U/mg of malate dehydrogenase per mg of protein at 50° C., it is unexpected that HB27/pTEXI-mdh, which contains two separate copies of the mdh gene, a wild-type mdh gene on the chromosome as well as the mdh gene on a plasmid vector, shows nearly the same activity (29.6 U/mg).

In this example, integration vectors were constructed that allow for "visual detection" of DNA fragments inserted into *Thermus* sp. chromosomes. Successful transformants are recognized by the loss of pigment due to insertional inactivation of the pigment gene. This provides for a reliable and convenient means of detecting and confirming the integration of homologous DNA into the chromosome of thermophilic hosts.

A *Thermus thermophilus* HB27 strain was constructed in which the phytoene dehydrogenase (phyD) gene was deleted. The ΔphyD colonies are recognized by a white colony phenotype. Wildtype phenotype is restored by transformation with *Thermus* plasmids containing an intact phyD gene. The wildtype phenotype provides a screening tool for the introduction of plasmid DNA into *Thermus* sp. and because phyD levels can be readily quantified, this host/vector system is a convenient tool for monitoring gene expression.

Figure 4:
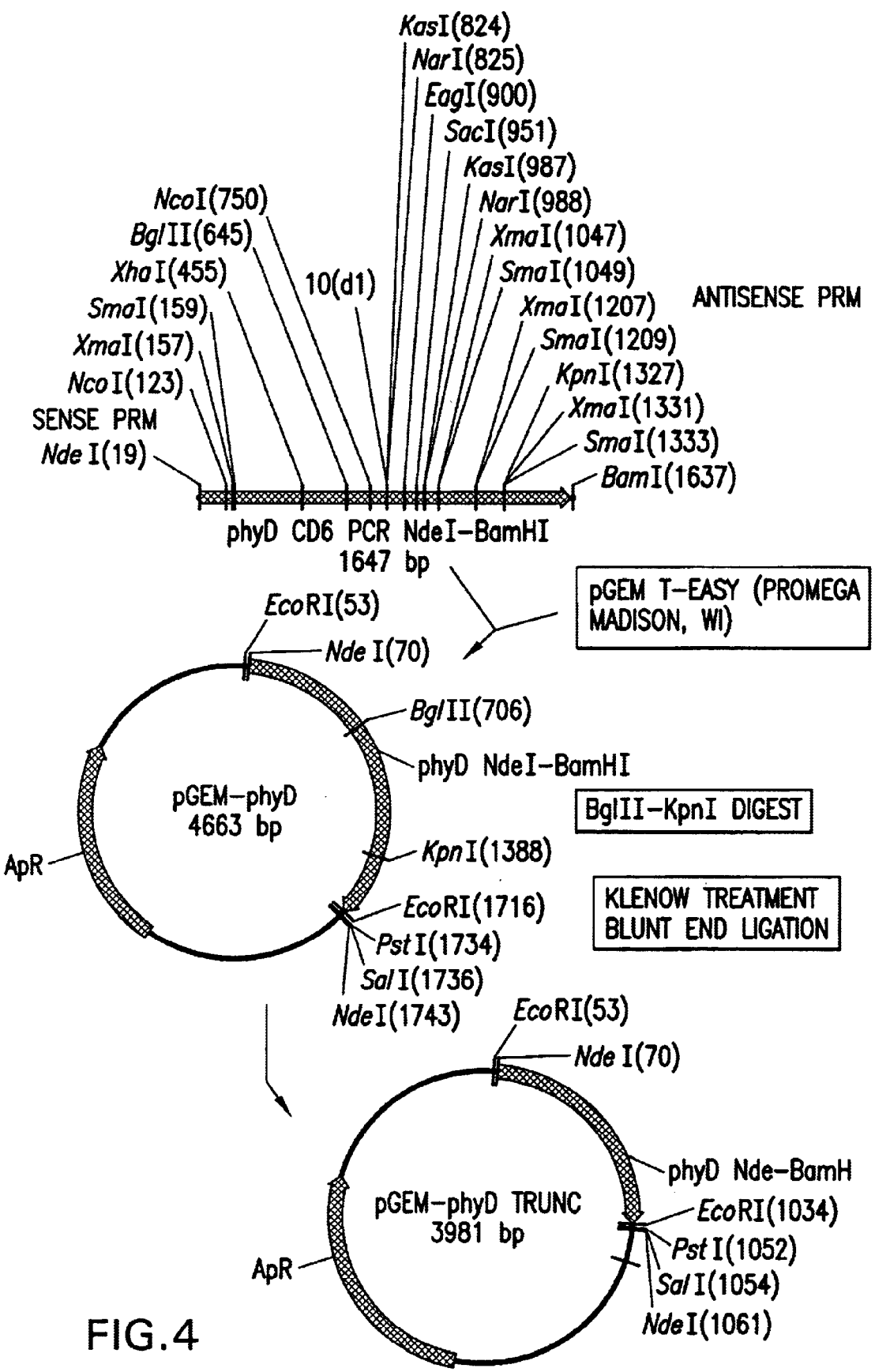
FIG. 4 illustrates the construction of an integrative vector used to delete the phyD gene from the chromosome of *Thermus* sp. More particularly.

To create the ΔphyD strain of *T. thermophilus* HB27, we constructed an integration vector designated pGEM-phyD trunc. The plasmid is detailed in FIG. 4. A PCR fragment containing the phyD gene was amplified from the *Thermus thermophilus* HB27 chromosome and cloned into pGEM T-easy. The pGEM-phyD construct was restriction enzyme digested with two unique restriction enzymes, BglII and KpnI. The restriction termini overhangs were blunted using a Klenow fragment of DNA polymerase I. The blunt ends were ligated to each other. The phyD gene is inactive. In the construction, the 3'-region of phyD and the 5'-region of phyD are left intact. Homologous recombination between phyD sequences allowed integration into the chromosome when it was used to transform *T. thermophilus* HB27. Transformants were screened at 55° C. on TT rich medium. Approximately $1 \times 10^2$ white colony transformants per µg DNA were observed.

Figure 5:
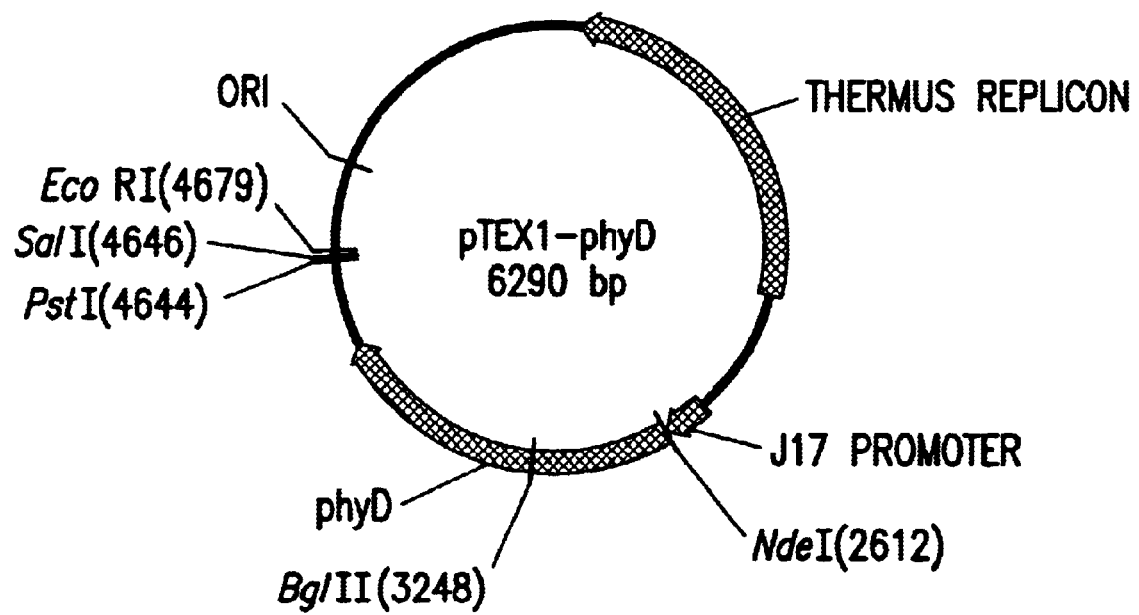
FIG. 5 shows the construction of a plasmid used to express the phyD gene in *Thermus* hosts in accordance with this invention. More particularly.

In this example, *Thermus* vectors containing phyD as a reporter gene were constructed. The phytoene dehydrogenase (phyD) gene from *Thermus thermophilus* HB27 was amplified by PCR and cloned into a *Thermus* and *E. coli* expression vector pTEXI. The expression vector pTEXI is capable of replication in both *Thermus* sp. and *E. coli*, and the promoter (J17) employed in this expression vector functions in both bacterial hosts. J17 is a constitutive promoter isolated from *T. thermophilus* chromosomal DNA. This expression vector containing the phyD gene, designated pTEXI-phyD, is diagramed in FIG. 5. A transcriptional termination sequence from the *T. flavus* phenylalanyl tRNA synthetase operon was cloned upstream of the cassette to prevent transcription read through from the native succinate-CoA ligase/phytoene dehydrogenase operon promoter.

A *T. thermophilus* ΔphyD strain was used where the native phyD had been interrupted using a truncated and inactive phyD gene as a host for *Thermus* plasmids expressing an intact phyD gene(pTEX1-phyD). The phyD gene can be used as a reporter gene to quantify promoter strength in *T. thermophilus*.

Figure 6:
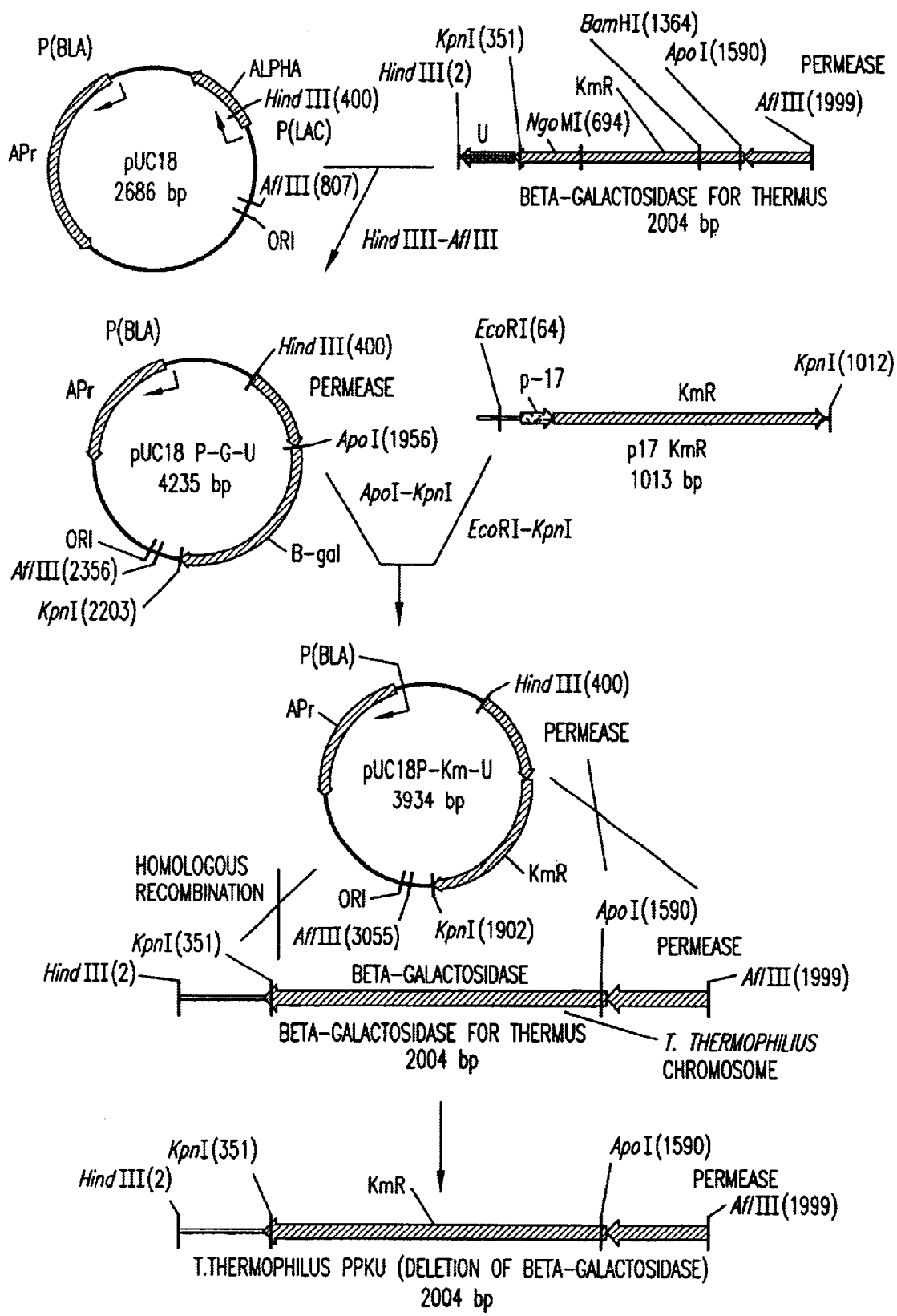
FIG. 6 illustrates the construction of *Thermus thermophilus* PPKU that contains a deletion of the β-galactosidase gene. More particularly.
Figure 7:
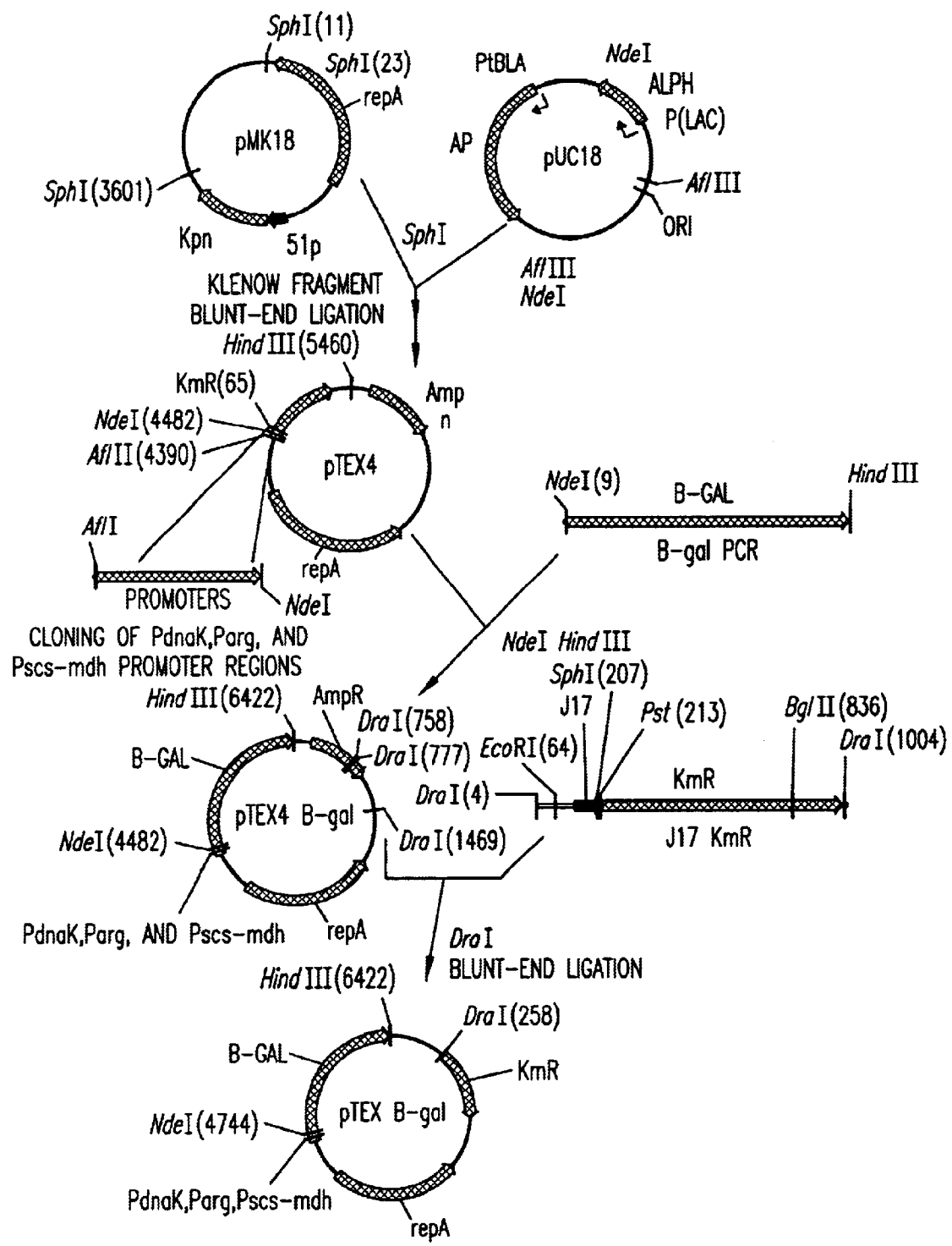
FIG. 7 shows the construction of a plasmid used to express β-galactosidase in *Thermus* species in accordance with one embodiment of this invention. More particularly.

In this example, a gene expression system (pTEX) for *Thermus thermophilus* HB27 was developed by using the β-galactosidase (β-gal) gene from *Thermus* A4 sp. as the reporter gene. A PPKU, *T. thermophilus* HB27 strain was constructed in which the β-gal gene was deleted in the chromosome using a double crossover integration vector, as shown in FIG. 6. To test the reporter system, two inducible promoters of PdnaK (coding for dnaK heat shock inducible protein induced by shifting the incubation temperature from 70 to 85° C.) and Parg (coding for unknown protein in arginine operon induced with the addition of arginine to the growth medium) and one carbon regulated promoter of key TCA cycle metabolic pathway genes, Pscs-mdh (coding for succinyl-coA and malate dehydrogenase) were cloned upstream of the reporter gene in pTEX in order to construct vectors pTEX7, pTEX8, and pTEX9 respectively, as shown in FIG. 7. These plasmids were transformed into *T. thermophilus* PPKU, a *Thermus thermophilus* HB27 Δβ-gal strain. Blue-green phenotype with X-gal containing agar is shown by transformation with *Thermus* plasmid vectors containing an intact *Thermus* A4 β-gal gene. Blue-green phenotype in a strain provides a visual screening tool for the introduction of plasmid DNA into *Thermus* sp. and the level of β-gal activity can be easily quantified, facilitating gene expression studies in *Thermus*.

The bacterial strains and plasmids used in this study are listed in Table 2.

TABLE 2

| Strain or Plasmid | Description |
| --- | --- |
| Bacterial strains | |
| E. coli DH5α | |
| T. thyermophilus HB27 | Wild type |
| Plasmids | |
| pMK18 | Thermus cloning vector |
| | Pslp promoter with Km gene |
| pUC18 | |
| pBGB3 | Thermus A4 sp. β-gal |
| pTEX1 | P17 promoter with Km gene |
| pTEX4 | NdeI cloning vector |
| | Pslp promoter with Km gene |
| pTEX7 | PdnaK promoter with β-gal gene |
| pTEX8 | pArg promoter with β-gal gene |
| pTEX9 | Pscs-mdh promoter with β-gal gene |

Thermus thermophilus HB27 was grown in TT rich medium (Lasa et al., "Development of Thermus-Eschericia Shuttle Vectors and Their Use for Expression of Clostridium Thermocellum celA Gene in Thermus Thermophilus" Journal of Bacteriology, 174:6424–6431,1992) and defined medium 162 (Degryse et al., "A Comparative Analysis of Extreme Thermophilic Bacteria Belonging to the Genus Thermus," Archives of Microbiology, 117:189–196, 1978). Arginine and uracil-free liquid medium with 20 mM pyruvate as the carbon source and 10 mM ammonium sulfate as the nitrogen source were employed for arginine induction experiments. Growth of T. thermophilus HB27 on single carbon sources was tested with minimal medium described in Fridjonsson et al., "The Structure of the Alpha-Galactosidase Gene Loci in Thermus brockianus IT1360 and Thermus thermophilus TH125", Extremophiles, 4:23–33, (2000). Escherichia coli DH5α was grown using nutrient broth or nutrient agar (Difco). Unless otherwise noted, kananycin was included in liquid or agar medium at 40 μg ml$^{-1}$ in experiments involving either T. thermophilus or E. coli cultures that were incubated at 55° and 37° C., respectively.

β-galactosidase specific activities are determined as follows. Cell-free extracts are prepared for the β-galactosidase activity tests by growing T. thermophilus HB27 cultures in TT media, at 55° C. overnight, until mid-to late-log phase growth is achieved. When heat-shock is employed, cell cultures are incubated for 10 min at 85° C. When arginine is added, cell cultures are induced during a 4-hour period. Cell pellets are harvested by centrifugation at 10,000×g for 10 minutes at room temperature, washed once with 0.1 M potassium phosphate (pH7.0) buffer and resuspended in same buffer. The cell suspensions are disrupted by sonication using a Branson 350 sonifier (Branson Sonifer Co., Danbury, Conn., USA) equipped with a microtip. The cell-free extracts are centrifuged at 10,000×g for 15 minutes at room temperature to remove cellular debris. β-galactosidase activity is determined using spectrophotometric assay according to the manufacturer's protocol (Promega). One unit of β-galactosidase activity is defined as 1 n mol o-nitrophenol liberated from o-nitrophenol-β-D-galactoside min$^{-1}$ at 37° C. Specific activity is expressed as β-galactosidase units (mg protein)$^{-1}$. Protein content is determined according to Smith, P. K. Et al., "Measurement of Protein Using Bicinchoninic Acid", Analytical Biochemistry. 150, 76–85 (1985). The BCA (bicinchoninic acid) protein assay reagent supplied with the system (Pierce Chemical Co., IL, USA) is used. Bovine serum albumin is used as a standard. β-galactosidase values are the averages of at least four experiments, with a variation of no more than 10% from the mean.

Recombinant techniques are standard unless otherwise noted (Sambrook et al., Molecular Cloning: A Laboratory Manual, Cold Spring Harbour, N.Y., 1989). Transformation of Thermus was carried out according to Koyama et al. "Genetic Transformation of the Extreme Thermophile Thermus thermophilus and of Other Thermus spp." Journal of Bacteriology 166:338–340, 1986. PCR amplification of the β-gal gene was performed with 1U of Taq DNA polymerase (Eppendorf), 20 ng of plasmid pBGB3, 0.25 μM concentration of each primer, a 25 μM concentration of dNTP mix (Life Technologies), and 1.5 mM MgCl$_2$ in the buffer recommended by the manufacture. Amplification was achieved with 25 cycles of 30 sec of denaturation at 94° C., 30 sec of annealing at 55° C., and 2 min of extension at 72° C., plus an additional extention at 72° C. for 7 min with a Perkin Elmer thermal cycler.

T. thermophilus HB27 containing pTEX7, pTEX8 or pTEX9 that have the β-gal gene under the control of promoters PdnaK, Parg, and Pscs-mdh, respectively, were used to study gene expression. The effect of temperature shock, arginine concentrations, and various carbon sources was determined using T. thermophilus HB27 containing pTEX7, pTEX8 or pTEX9, respectively. Detection of β-galactosidase activity performed with recombinant strains demonstrated that the reporter gene produced a functional β-galactosidase in T. thermophilus HB27. β-gal activity in the arginine promoter construct increased from 6.5 U/mg to 9.75 U/mg after arginine addition and the dnaK operon promoter construct increased from 5.2 U/mg to 10.4 U/mg after heat shock induction. The different level of β-galactosidase activity has been demonstrated in the growth of diverse carbon sources with scs-mdh promoter construct (pTEX9). These results validate the usefulness of these vectors for gene expression studies in Thermus and have contributed toward the development of a valuable thermophilic host/vector expression system.

In this example, a T. thermophilus HB27 host/vector expression system is constructed. A series of promoters were cloned upstream of Thermus A4 β-galactosidase gene in order to test the newly developed reporter system. FIG. 7 summarizes the construction of the reporter system and the three test vectors developed in this study. Each promoter region was amplified by a PCR reaction (Table 3). Amplified promoters were cloned into pTEX4. A 1983-bp β-gal gene from Thermus A4 spp. was amplified from pBGB3 vector using the following PCR primers: forward β-gal 5'-ACACACCATATGCTCGGCGTTTGCTATTACC-3' (SEQ ID NO: 1) and reverse β-gal 5'-GCGGCAGACCCGCCGCCGTACAAGCTTACACAC-3' (SEQ ID NO: 2). Restriction sites were added into the PCR primers to give 5'NdeI and 3'HindIII sites. The β-gal gene PCR product was cloned into pTEX7, pTEX8, and pTEX9 vectors, respectively. Km$^R$ gene cassette from pTEX1 was amplified by PCR using the following PCR primers: forward Km$^R$ 5'-ACACACTTTAAACATGGCCTAATGCCACCC-3' (SEQ ID NO: 3) and reverse Km$^R$ 5'-TTGTGTTTTAAATCAAAATGGTATGCGTTT-3' (SEQ ID NO: 4) and cloned into pTEX7, pTEX8, and pTEX9, respectively (FIG. 7).

TABLE 3

Primers for Amplification of Promoter Regions.

| Promoters | | Primers |
|---|---|---|
| PdnaK | Forward | ACACACCTTAAGGGGTGTCCCCGGCGCGC (SEQ ID NO: 5) |
| | Reverse | ACACACCATATGACGTCTTCACCTCGCC (SEQ ID NO: 6) |
| Parg | Forward | ACACACCTTAAQGCTTAAGGAATTCTGGCCGCC (SEQ ID NO:7) |
| | Reverse | ACACACCATATGCCTTATCACCTTCCTTTT (SEQ ID NO: 8) |
| Pscs-mdh | Forward | ACACACCTTAAGAATTGCTGGATGGCCTC (SEQ ID NO: 9) |
| | Reverse | ACACACCATATGGACCCACCTCCCTTGCCG (SEQ ID NO: 10) |

Restriction sites were added into the PCR primers to give 5'AflII and 3'NdeI sites.

In this example, a β-galactosidase mutant is constructed by double crossover for use as a recipient strain. To use *T. thermophilus* HB27 for expression of heterologous and homologous β-galactosidase, the β-gal gene was inactivated. An integration cassette was constructed in which the β-galactosidase gene was insertionally inactivated in vitro with a gene (kan) encoding a thermostable kanamycin resistance protein. By the construction, the 3'-region of β-gal and the 5'-region of β-gal were left intact to allow sequences for homologous recombination, but the middle of the gene was deleted. The *T. thermophilus* HB27 was transformed with a suicide integration vector and transformants were selected on kanamycin plates incubated at 55° C. Because suicide vectors cannot replicate in *Thermus*, resistant colonies should be those in which the integration cassette has inserted into the chromosome by homologous recombination between the β-gal flanking sequences in the plasmid and the chromosome. To verify the integration of the kan gene into the β-galactosidase gene locus, chromosomal DNA from a transformant strain and the wild type were extracted and analyzed by PCR. Expected fragments were amplified according the length in FIG. 6. The molecular analysis revealed the insertion of kan into the β-gal locus by homologous recombination, via double crossover, creating the mutant strain PPKU.

Figure 8:
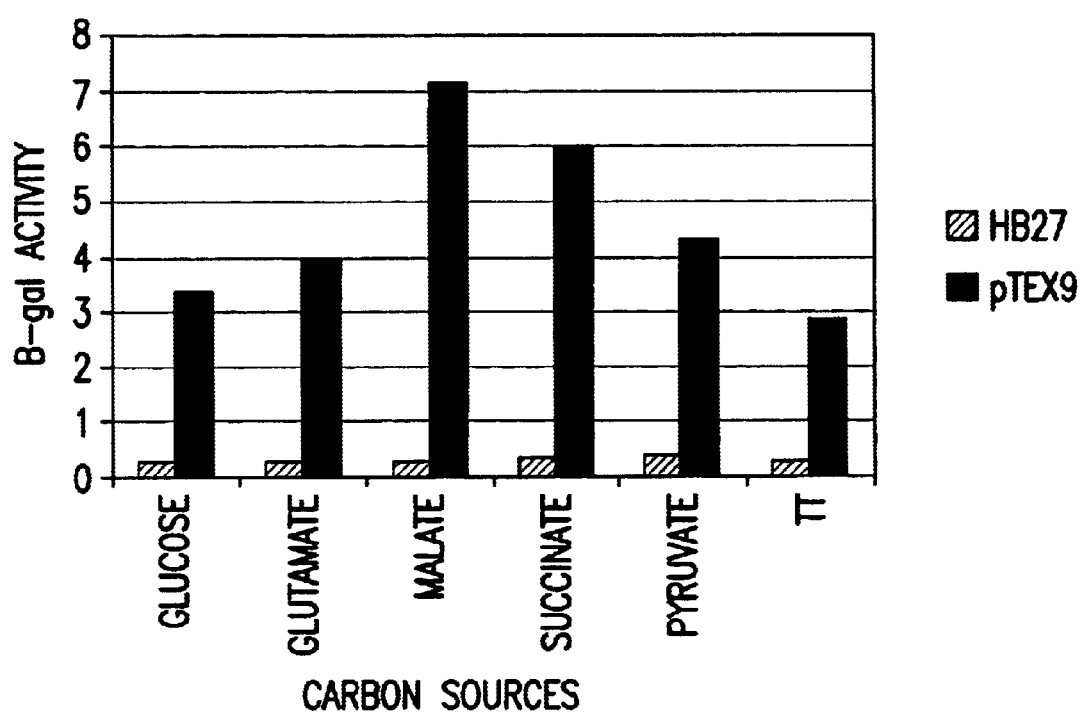
FIG. 8 illustrates the levels of β-galactosidase produced by *T. thermophilus* HB27 with and without pTEX9, a plasmid containing the β-galactosidase gene under the control of the promoter Pscs-mdh. The level of β-galactosidase is increased in cells containing pTEX9 and levels vary in different carbon sources reflecting the inducibility of the Pscs-mdh promoter.

Since the presence of glucose notably influenced the level of mdh gene expression in *E. coli*, we examined how carbon compounds affect the Pscs-mdh promoter-β-gal gene expression. β-gal expression under the control of the Pscs-mdh promoter varied over a 2.5-fold range (FIG. 8). Expression was lowest when a glucose medium was used and highest when malate was used as the carbon source. Expression of the mdh gene is under catabolite control like *E. coli* by carbon type.

Figure 9:
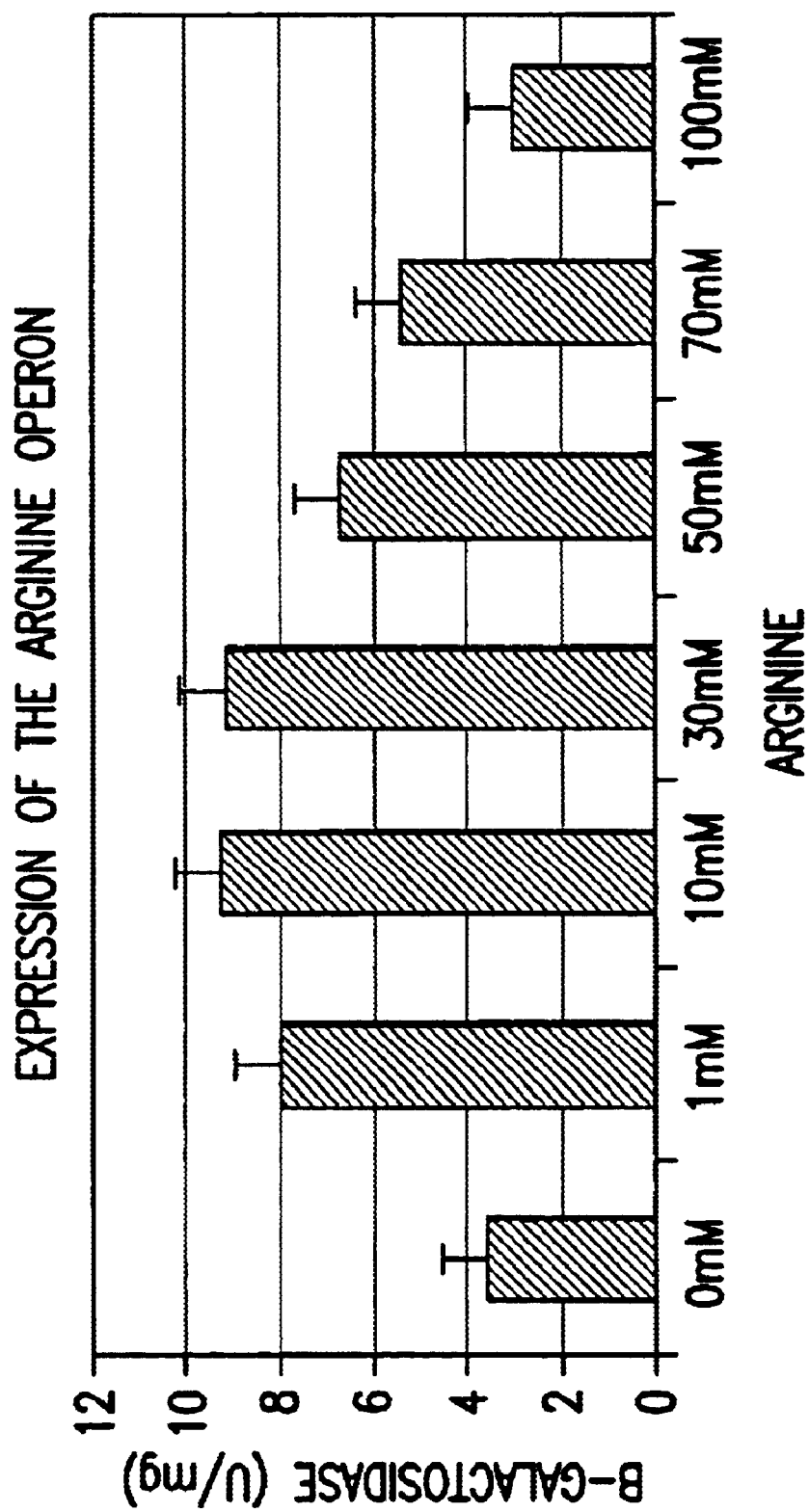
FIG. 9 is a diagram showing the induction of β-galactosidase activity of the Parg::β-gal fusion in pTEX8 by increasing arginine concentration in the growth medium. The plasmid pTEX8 contains the β-galactosidase gene under the control of the Parg promoter, which is induced by arginine up to a concentration of 30 mM, but higher arginine concentrations decrease the activity of this promoter.

*T. thermophilus* HB27/pTEX8 was grown in arginine and uracil-free liquid medium to an $OD_{600}$ of 0.6, and then various concentrations of arginine were added and the cultures were incubated 120 min at 65° C. The β-galactosidase activities measured on crude extracts obtained from these cultures are shown in FIG. 9. An optimal concentration of arginine which induced expression of the parg::β-gal fusion was 10 mM.

An object of this invention is to develop an efficient gene expression reporter system for *T. thermophilus* HB27. We examined the β-gal gene from *Thermus* A4 sp. to determine whether it could be used as a reporter gene. Detection of β-galactosidase specific activity after this reporter gene was introduced on a plasmid indicated that the β-galactosidase produced by the new reporter system was functional. This was confirmed by the 10–100 fold increase in β-galactosidase specific activities in strains containing the Pdnak, Parg, or Pscs-mdh promoters upstream of the reporter gene. The substantial differences in specific activity between the reporter systems with and without *Thermus* promoters also suggest that the sensitivity of the reporter system is adequate to monitor even weak promoters.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

We claim:

1. A method for introducing and stabilizing heterologous and recombinant genes in a thermophilic host comprising the steps of:

inactivating or deleting a malate dehydrogenase gene from said thermophilic host, resulting in a modified thermophilic host having a reduced growth rate; and inserting a DNA fragment of interest into said modified thermophilic host together with an intact said malate dehydrogenase gene, whereby host growth rate defined by said characteristic gene is restored to said thermophilic host thereby enabling detection or confirmation of successful transformation using plasmid vectors or integration of said DNA fragment into a chromosome of said thermophilic host.

2. A method in accordance with claim 1, wherein said thermophilic host is a *Thermus* sp.

3. A method in accordance with claim 1, wherein said thermophilic host is *Thermus thermophilus*.

4. In a *Thermus* strain comprising an inactivated or deleted malate dehydrogenase gene, a method for producing biotechnology products comprising the steps of:

cloning a gene of interest into at least one convenient multiple cloning site of a plasmid or integration vector comprising an intact said malate dehydrogenase gene, at least one *Thermus* promoter and said at least one convenient multiple cloning site;

transforming said *Thermus* strain with said plasmid or integration vector; and expressing said gene of interest in said *Thermus* strain using said *Thermus* promoter.

* * * * *